United States Patent
Connelly et al.

[19]

[11] Patent Number: 5,938,932
[45] Date of Patent: Aug. 17, 1999

[54] HIGH-THROUGHPUT METHOD AND APPARATUS FOR IDENTIFYING, QUANTITATING AND DETERMINING THE PURITY OF CHEMICAL COMPOUNDS IN MIXTURES

[75] Inventors: James A. Connelly, Falls Township, Pa.; Linda O'Brien, Spotswood, N.J.; Sue Xiuqing Zhang, Somerset, N.J.; Ning Zhao, West Windsor, N.J.

[73] Assignee: Pharmacopeia, Inc., Princeton, N.J.

[21] Appl. No.: 08/970,941

[22] Filed: Nov. 14, 1997

[51] Int. Cl.⁶ .................................................. B01D 15/08
[52] U.S. Cl. ...................... 210/659; 210/656; 210/198.2; 73/61.52; 436/161
[58] Field of Search ..................................... 210/635, 656, 210/659, 198.2; 73/61.52, 61.58; 436/161

[56] References Cited

U.S. PATENT DOCUMENTS

| | | | |
|---|---|---|---|
| 4,840,730 | 6/1989 | Saxena | 210/659 |
| 5,234,586 | 8/1993 | Afeyan | 210/198.2 |
| 5,670,054 | 9/1997 | Kibbey et al. | 210/656 |
| 5,766,481 | 6/1998 | Zambias | 210/659 |

FOREIGN PATENT DOCUMENTS

WO 96/40398  12/1996  WIPO .................................. 210/659

*Primary Examiner*—Ernest G. Therkorn
*Attorney, Agent, or Firm*—DeMont & Breyer, LLC

[57] ABSTRACT

A method and apparatus for high-throughput identity confirmation, quantitation and purity determination of a compound of interest in a mixture of compounds is disclosed. According to the method, a chemical mixture, such as may be obtained from a chemical library, is processed to obtain a stream having a time-varying composition, such as by using a high pressure liquid chromatograph. The stream is split into two portions or streams for substantially contemporaneous detection in a compound-identifying device, such as a mass spectrograph, and in a compound-quantitating device, such as an evaporative light scattering detector. A peak in a chromatogram obtained from the compound-quantitating device is identified as the compound of interest by cross-correlation, via elution time, with chromatographic results obtained from the compound-identifying device. Once the peak is identified as corresponding to the compound of interest, the corresponding peak area is used for quantitation and purity determination.

11 Claims, 4 Drawing Sheets

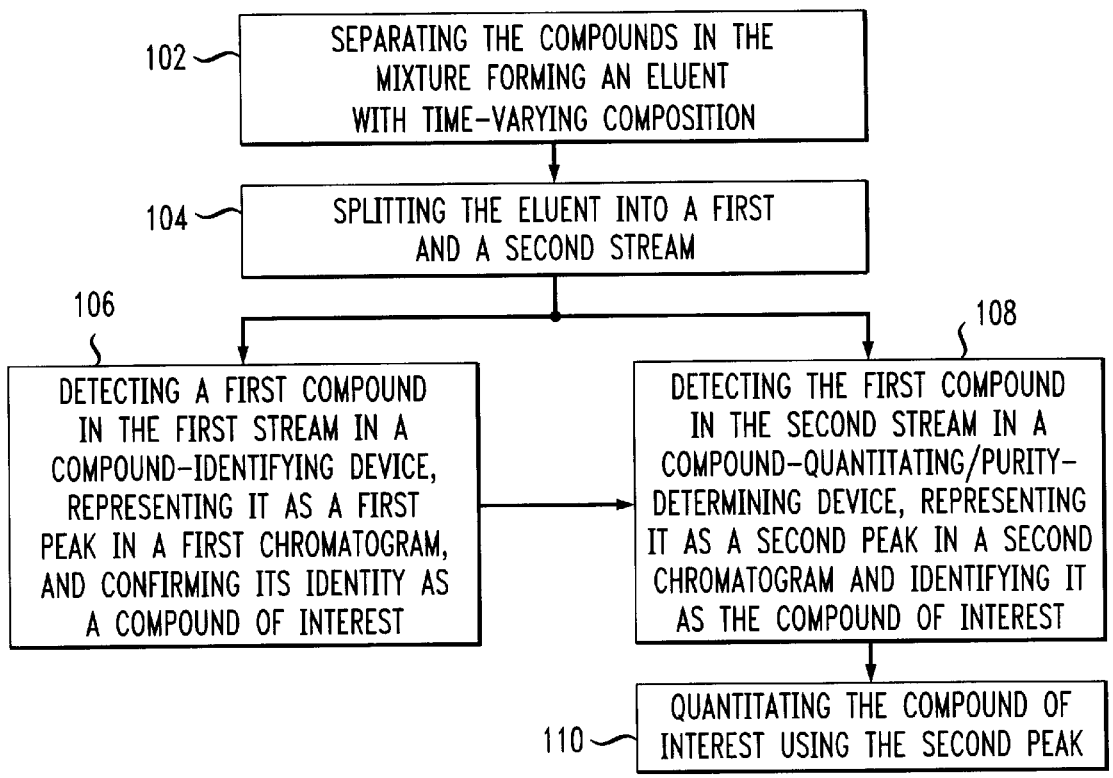
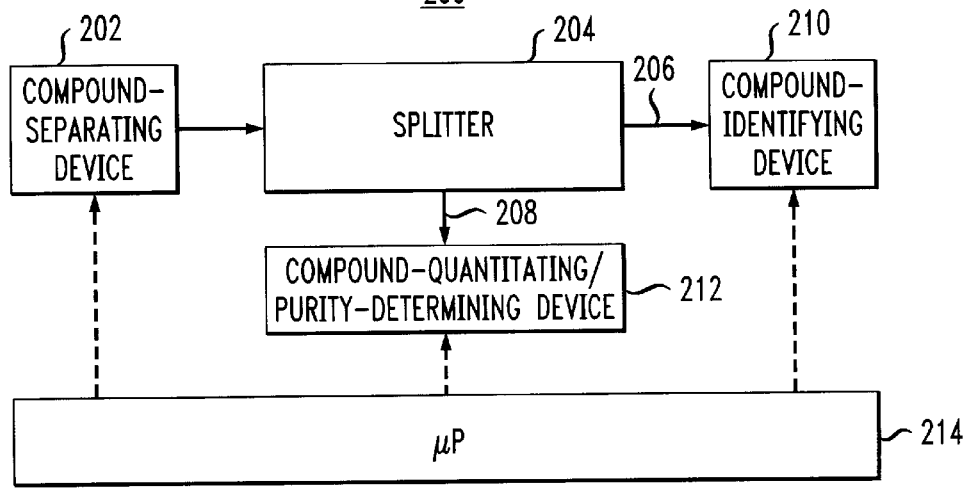

HIGH-THROUGHPUT METHOD AND APPARATUS FOR IDENTIFYING, QUANTITATING AND DETERMINING THE PURITY OF CHEMICAL COMPOUNDS IN MIXTURES

FIELD OF THE INVENTION

The present invention relates to analytical chemistry. More particularly, the present invention relates to a method and apparatus for confirming the identity and determining the purity and quantity of a chemical compound in a mixture of other compounds.

BACKGROUND OF THE INVENTION

Chemical libraries, such as combinatorial chemical libraries, comprise chemical compounds that have been synthesized from a systematic series of reactions. Such libraries can include an extraordinarily large and varied collection of compounds. Large chemical libraries are typically used to screen for biological activity, such as for pharmaceutical and agricultural purposes, among others.

Chemical libraries are typically created by either "parallel synthesis" or "split synthesis." In the former method, different compounds are synthesized in separate vessels. A commonly used format for parallel synthesis is the 96-well microtiter plate. An automated process can be used for adding different reagents to separate wells of the plate in a predefined manner to produce a chemical library.

In the split synthesis method, compounds are assembled on the surfaces of polymeric resin beads or other solid supports by an iterative process. In particular, a sample of beads is divided among several reaction flasks, and a different compound or "chemical building block" is added to each flask. The chemical building blocks link to the beads, one to each bead. The beads from all the containers are pooled, divided into a new set of reaction flasks, and a different chemical compound is added to each container. The added compound reacts with the building blocks already linked to each bead. The beads are again pooled, divided and a new group of compounds are added, one to a container. Reaction occurs, and the process is repeated as desired. A very large and diverse chemical library may be obtained after relatively few such iterations.

Comparing the methods, split synthesis typically yields relatively smaller quantities of a relatively larger number of compounds, whereas parallel synthesis generates relatively larger quantities of a relatively smaller number of compounds. Constructing a library by either method may involve determining and optimizing reaction conditions to yield desired products, analyzing reaction products to assure that desired products are obtained, as well as determining the yield and purity of such products.

Whether optimizing a large split-synthesis-derived chemical library, or simply analyzing the products of a large parallel synthesis-derived chemical library, the time and resources expended for qualitative and quantitative analysis thereof is substantial. While conventional chemical analysis techniques and devices can be used for analyzing chemical libraries, such methods are, in practice, unworkable, when the library contains a large number of compounds.

It is known in the art that an evaporative light scattering detector (ELSD) may be advantageously used in conjunction with high performance liquid chromatography (HPLC) to quantitate compounds associated with chemical libraries. ELSD is particularly well suited to the quantitation (e.g., yield determination, etc.) of individual compounds of chemical libraries because it is a "universal" detector, i.e., its response is substantially independent of specific physical or chemical properties of the compound being analyzed. As such, the ELSD response may be calibrated by a single standard, rather than a large number of reference standards corresponding to each compound being analyzed, which, for large chemical libraries, would be unworkable.

Note that unlike the ubiquitous UV absorbance detector, the response of the ELSD is not dependent on the presence of a chromophore in the analyzed compound. Chromophores vary from compound to compound, and the UV absorbance detector responds differently to different chromophores. As such, a large number of standards are disadvantageously required when using a UV absorbance detector for analyzing a large number and variety of compounds. Moreover, chromophores may be absent in many of the compounds present in chemical libraries, frustrating the detection of such compounds via UV absorbance. For additional background concerning the shortcomings of common analytical techniques as applied to the identification, purification and quantification of chemical libraries, see U.S. Pat. No. 5,670,054, incorporated by reference herein.

An example of using ELSD in a technique for identifying, purifying and quantitating library-derived chemical compounds is provided by Kibbey et al. in the aforementioned U.S. Pat. No. 5,670,054. According to the patent, a first HPLC column is used in conjunction with a mass spectrograph to characterize compounds present in a mixture. The chromatographic and mass spectroscopic data generated by the mass spectrograph are used to purify several compounds of interest from the mixture through a system including a second HPLC column and a UV absorbance detector. Finally, the concentration of each compound of interest, as purified, is estimated using a system that includes an HPLC column and an ELSD.

While advantageously using an ELSD for quantitation, the Kibbey et al. method for purifying chemical-library-derived compounds requires multiple runs through different HPLC columns connected to different analytical devices. While such an approach does appear to provide a way to purify library-derived compounds, it does not provide the art with a high-throughput method for rapid analysis of a large number of compounds, such as is useful, for example, for optimizing and/or analyzing chemical libraries. Until now, such a method and system has been unavailable.

SUMMARY OF THE INVENTION

A method and apparatus for high-throughput analysis of a chemical mixture, such as may be obtained from a chemical library, is disclosed. According to the invention, a chemical mixture, including at least one compound of interest, is processed to separate constituent chemical compounds "in time," thereby forming a product stream or eluent with a time-varying composition. Such separation may be accomplished by a device utilizing, for example, a chromatographic separation technique. The eluent is advantageously split into a first and second stream for substantially contemporaneous, high-throughput detection.

The first stream is sent to a first analytical device, in particular, a compound-identifying device. The compound-identifying device is operable, in the present invention, to confirm the presence of a compound of interest. The compound-identifying device, which in one embodiment is a mass spectrograph, detects the presence of the compound of interest and other compounds in the first stream and represents them, in a first chromatogram, as a plurality of peaks having characteristic elution times. The second stream is sent to a second analytical device, in particular, a compound-quantitating/purity-determining device. The compound-quantitating/purity-determining device is operable, in the present invention, to quantitate and determine the purity of the compound of interest. The compound-quantitating/purity-determining device detects the presence the compound of interest and other compounds in the second stream and represents them, in a second chromatogram, as a second plurality of peaks having characteristic elution times. Preferably, the compound-quantitating/purity-determining device is a universal detector. Such a detector is substantially insensitive to physical or chemical differences in compounds being tested so that a single standard can be used for calibration. In one embodiment, an evaporative light scattering detector ("ELSD") is used.

While peaks appearing in second chromatogram provide quantitative information about the compounds in the second stream, they are not directly identifiable as representing a specific compound. In an important aspect of the present invention, the two detecting operations described above in the two analytical devices advantageously occur at substantially the same time, so that the elution times for a given compound appearing in both the first and second chromatograms are substantially identical, or have but a small, fixed, readily-determined offset. As such, peaks appearing in the second chromatogram can be readily identified as corresponding to a particular compound by matching their elution times to the elution times obtained from the first chromatogram, using appropriate software.

Deviations in system attributes that might otherwise occur in separate runs, e.g., differences in the solid stationary phase, operating conditions and the like, are advantageously avoided in a method and apparatus in accordance with the present invention. Such uniformity of conditions contributes significantly to the accuracy of cross correlating elution times for two analytical devices.

The present invention thus provides a way to unambiguously correlate compound identity between different analytical devices. Additionally, by performing compound confirmation and quantitation/purity determination in parallel operations, analysis is performed at a hitherto unattained rapid rate.

BRIEF DESCRIPTION OF THE DRAWINGS

Further features of the invention will become more apparent from the following detailed description of specific embodiments thereof when read in conjunction with the accompanying drawings, in which:

FIG. 1 is a flow diagram illustrating a method according to the present invention;

FIG. 2 shows an exemplary apparatus for carrying out the present method;

DETAILED DESCRIPTION OF THE INVENTION

Figure 3:
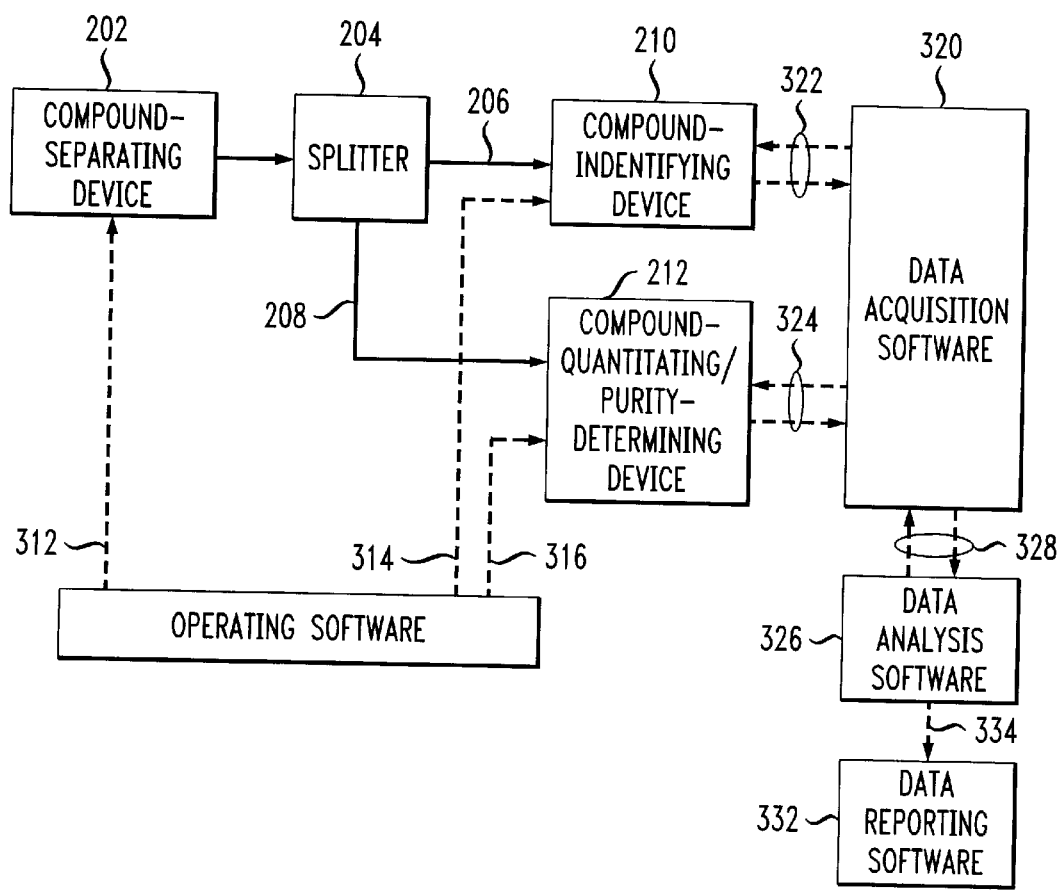
FIG. 3 shows a conceptual illustration of a manner in which software controls the devices comprising the apparatus of FIG. 2, acquires and anaylzes data, and reports information.

Exemplary embodiments of a method 100 according to the present invention, and an apparatus 200 for carrying out that method, are illustrated, respectively, in FIGS. 1 & 2. In operation block 102 of the flow diagram shown in FIG. 1, a plurality of compounds forming a first mixture are separated "in time" so that an eluent comprising the same compounds, but having a time-varying composition, is formed. Apparatus 200 (FIG. 2) includes a compound-separating device 202 for accomplishing the operation 102. In one embodiment, the compound-separating device 202 is a chromatographic device, such as a high performance liquid chromatograph ("HPLC"). A gas chromatograph ("GC") could be used, as well.

As is well known in the art, chromatographic methods rely on differential adsorption/desorption rates of compounds on a solid stationary phase. The solid stationary phase is typically disposed in a vessel such as a column. Individual compounds comprising the mixture traverse the column at different rates due to the differences in the adsorption/desorption rates of the various compounds. In an alternative embodiment, capillary electrophoresis may be used for separating the compounds.

Thus, as a result of operation 102, the constituent compounds of the mixture are "separated" forming an eluent with a time-varying composition. As indicated in operation block 104, the eluent is split, such as by the splitter 204, into two streams to facilitate simultaneously detecting the aforementioned constituent compounds in two different types of detectors. The information obtained from the two detectors is used to identify, quantitate and determine the purity of at least one compound of interest in the eluent. In one embodiment, the eluent is apportioned at least about 75 volume percent to a second stream for compound quantitating and purity determination, and less than about 25 volume percent to a first stream for compound identification. In other embodiments, the eluent may be apportioned differently, as is suitable for the equipment being used.

As used herein, the term "identifying" means confirming the presence of a compound of interest in a mixture. In other words, the presence of the compound of interest in the mixture is expected, but must be confirmed. The term "quantitating," as used herein, means determining the amount of the compound of interest in a mixture of other compounds. When the mixture is a reaction product of a known quantity of reactants, compound yield may be determined in this fashion.

As indicated in operation block 106, the compound of interest is identified in the first stream. Such identification is accomplished by delivering the first stream, via conduit 206, to a compound-identifying device 210. The compound-identifying device detects the compound of interest and other compounds in the first stream. In conjunction with appropriate software, the detected compounds are represented as a first chromatogram including a first plurality of peaks extending above a baseline. In such chromatograms, the ordinate defines the "intensity" of the peak, and the abscissa is expressed as "retention time." Since the eluent has a time-varying composition due to action of the compound-separating device 202, the peaks corresponding to the different compounds are positionally separated on the chromatogram. Ideally, each peak corresponds to a different one of the compounds in the first stream. The plurality of peaks includes a first peak corresponding to the compound of interest.

In one embodiment, the compound-identifying device 210 is a mass spectrograph, although other devices known in the art, such as a nuclear magnetic resonance (NMR) spectrograph, or devices giving elemental analysis, such as an atomic emission detector (AED), may suitably be used. The mass spectrograph provides a molecular weight for each of the peaks, i.e., each of the compounds in a sample.

In one use for the present invention, a particular compound of interest is expected to be present in the mixture being analyzed. Thus, as previously indicated, the "identification" step is actually a "confirmation" or "verification" of that particular compound's presence. For embodiments in which a mass spectrograph is used as the compound-identifying device 210, a peak is identified as corresponding to, and confirming the presence of, the compound interest when its mass spectrograph-determined molecular weight matches the (known) molecular weight of the compound of interest. Such matching may be performed via appropriate software. Such software, its integration with the detectors, and various operations performed thereby are described later in this specification.

In operation block 108, the compound of interest and other compounds in the second stream are detected using a compound-quantitating/purity-determining device 212. In conjunction with appropriate software, the detected compounds are represented as a second chromatogram including a second plurality of peaks extending above a baseline. An area underneath each peak ("peak area") in the second chromatograph is correlatable to the amount of a compound (corresponding to the peak) present in the mixture.

The device 212, which receives the second stream for detection via conduit 208, is preferably a "universal" detector. A universal detector is defined herein as a detector having a response that is substantially independent of the specific physical or chemical attributes of a compound being detected. Such detectors may advantageously be calibrated to acceptable accuracy using a single standard. As previously mentioned, an UV absorbance detector is not a universal detector.

In one embodiment, an evaporative light scattering detector ("ELSD") is used as the compound-quantitating/purity-determining device 212. For background information pertaining to ELSD, see Peterson et al., "Validation of an HPLC Method for the Determination of Sodium in LY293111 Sodium, a Novel LTC Receptor Antagonist, Using Evaporative Light Scattering Detection," J. Liquid Chromatography, 18(2), pp. 331–338 (1995). In a second embodiment, the compound-quantitating/purity-determining device 212 is a chemiluminescent nitrogen detector. Both the ELSD and the chemiluminescent nitrogen detector are universal detectors.

To obtain the best performance using an ELSD in conjunction with HPLC, the HPLC "method" should be applicable to a wide range of compounds. To that end, a single general broad solvent gradient HPLC method should be used for all samples. Using such a broad solvent gradient method aids in providing satisfactory resolution for compounds over a broad polarity range. Moreover, ELSD operating conditions, including the gain and gas pressure and temperature, should be fixed and constant.

As previously noted, the peak area for each peak in a chromatogram obtained from an compound-quantitating/purity-determining device 212, such as an ELSD, provides an indication of the relative amounts of the corresponding compounds in the eluent. It is known that the correlation between peak area and compound amount is not linear for the chromatogram obtained from an ELSD. In particular, the relationship between area and amount or mass is given by:

$$\log A = a \log m + b,\qquad [1]$$

where: A is the peak area, m is the amount of the compound corresponding to the peak and a & b are constants.

Notwithstanding the aforementioned nonlinear relationship, those skilled in the art typically calculate compound purity using peak area, rather than the amount of the compound. That is, purity P (expressed in percent) is conventionally calculated according to the expression:

$$P=(A_i/\Sigma A_i)\times 100.$$

The inventors have discovered that a more accurate estimate of purity may be obtained using the expression:

$$P=(m_i/\Sigma m_i)\times 100. \qquad [2]$$

The constants "a" and "b" are weakly dependent upon the compound being analyzed. One approach that has been found to be satisfactory in accounting for such dependence is to randomly select a number of compounds from a chemical library of interest, and then run each compound through the compound-quantitating/purity-determining device and calculate "a" and "b" according to expression [1]. The calculated values of "a" and the calculated values of "b" are averaged, and the averaged values of "a" and "b" are used for quantitation and purity determination for each compound of interest in the library.

The compound-quantitating/purity-determining device 212, e.g., an ELSD, does not provide any direct indication of the identity of quantitated compounds. To address that problem, peak detection in the compound-identifying device 210 and peak detection in the compound-quantitating/purity-determining device 212 are carried out substantially contemporaneously according to the present invention. As a result, a peak corresponding to a given compound advantageously appears at substantially the same elution time or position in the chromatograms obtained from both the compound-quantitating/purity-determining device 212 and the compound-identifying device 210. Thus, the peaks appearing in the chromatogram generated by the compound-quantitating/purity-determining device 212, which provide only quantitative information, can be readily identified as corresponding to a particular compound based on the identity/elution time results obtained from the compound-identifying device 210.

In preferred embodiments, the tasks of operating the various analytical devices comprising the present apparatus, obtaining and analyzing data obtained therefrom, and reporting the data, are performed by an appropriately-programmed general purpose processor or hardwired special-purpose processor 214. It should be understood that the present apparatus can be operated without a processor that coordinates and performs all such functions.

FIG. 3 provides a conceptual or functional illustration of the various tasks provided by the software advantageously used in conjunction with the present invention. Operating software 310, typically available from the vendor of a piece of analytical equipment, may be used to control some or all of the various analytical devices comprising the present apparatus. The software can be internal to each device, or, alternatively, such software can be resident in the processor 214, such as a "personal computer," that "externally" controls operation of the devices in an integrated manner. In particular, the operating software can be used to operate the compound-separating device 202, the compound-identifying device 210 and the compound quantitating/puritydetermining device 212, as indicated via control lines 312, 314 and 316.

Data acquisition software 320, typically available from an equipment vendor, is operable to request and receive data obtained by the compound-identifying device 210 and the compound-quantitating/purity determining device 212, as is illustrated by respective data lines 322 and 324. Data analysis software 326 is used for analyzing the data obtained from the analytical instruments 210, 212. The data analysis software 326 includes both "standard" or "off-the-shelf" software for providing analytical results routinely obtained for a particular type of analytical device, as well as user-definable software for providing analysis unique to the present invention. After requesting and receiving data from the data acquisition software 320 over data line 328, the appropriately-coded user-definable software performs, in accordance with the present invention, the operations of confirming the presence of the compound of interest, quantitating the compound and determining its purity. Such operations are described further below in conjunction with the flow diagram shown in FIG. 4. Finally, the data reporting software 332 receives, via data line 334, the results of the data analysis and presents it in a user-defined format providing information of interest to the user.

It should be understood that four "separate" software packages are not necessarily required to accomplish the above-described tasks of (i) operating the analytical devices and (ii) acquiring, (iii) analyzing and (iv) reporting data. For example, software packages capable of operating analytical devices, acquiring data therefrom, and doing at least some analysis of such data are readily available from vendors of analytical equipment. One such software package is available from PE Sciex, subsidiary of The Perkin Elmer Corporation, as MassChrom™ data software. It should be appreciated, therefore, that the various data communication lines running between various "packages" of software, i.e., lines 328 & 334, do not exist physically, but, rather, are metaphorical in nature and are used simply for clarity of illustration.

In accordance with the present invention, the software is operable to associate the peaks from two different pieces of analytical equipment to quantitate and determine the purity of a compound of interest. To do so, the software must "ask" specific questions about the data, and perform certain matching tasks not performed by any "off-the-shelf" software package. Thus, as previously noted, a second "user-definable" software package will typically be required for use in conjunction with the aforedescribed operating/data acquisition/basic analysis software. Such a package is available from PE Sciex, for example, as AppleScript™, for use with Apple Computers.

Figure 4:
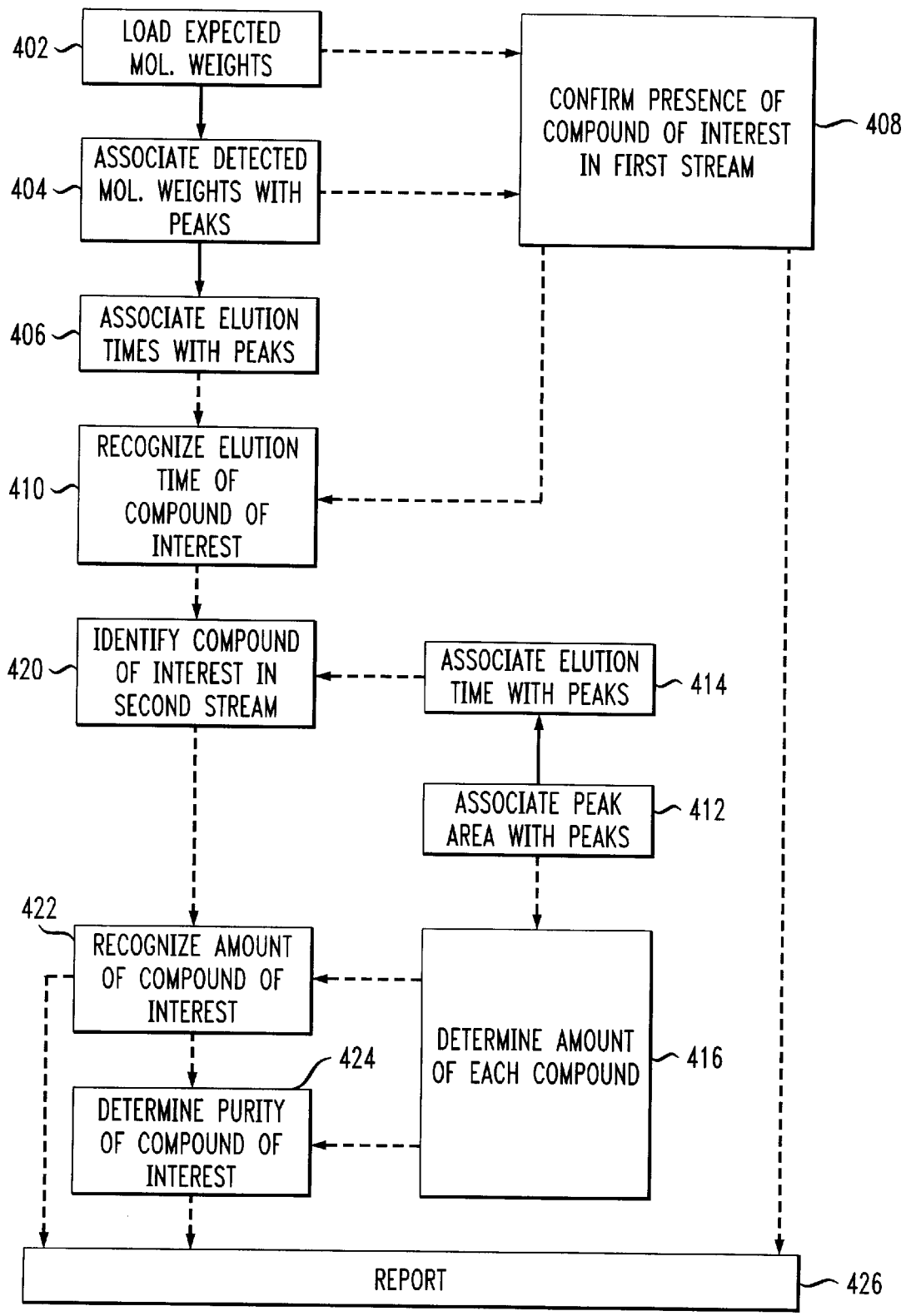
FIG. 4 shows a basic flow chart for data analysis operations.

FIG. 4 is a flow chart showing an exemplary embodiment of a method in which data obtained from the compound-identifying device 210 and the compound-quantitating/purity determining device 212 is processed, according to the present invention, to identify, quantitate and determine the purity of a compound of interest. For the purposes of the following description, the compound-identifying device 210 is assumed to be a mass spectrograph, and the compound-quantitating/purity determining device 212 is an ELSD. It should be understood that if different analytical devices are used, then the operations shown in FIG. 4 may require suitable modification. For example, if a device other than a mass spectrograph is used, then the operation of block 404, i.e., associating detected molecular weights with peaks, may require modification to associate some other characteristic with the peaks.

In operation block 402, the molecular weight of each of any number of compounds of interest expected to be present in the sample(s) being analyzed are loaded in a processor-accessible storage or memory device. In block 404, the molecular weights detected by the compound-identifying device 210 are associated with the various specific peaks appearing in a first chromatogram obtained from that device, and stored in memory. As indicated in block 406, elution times are likewise associated with each of the aforementioned peaks and stored in memory, as well. Thus, molecular weight and elution time is available for each peak in the first chromatogram, i.e., for each compound in the sample. In block 408, the presence of a compound of interest is confirmed. To do so, detected molecular weights are compared against the molecular weights stored in memory in block 402. If a match is obtained, and the amplitude of the peak possessing the matched molecular weight exceeds a certain predefined threshold, the presence of the compound is confirmed. Having identified a peak as corresponding to, and confirming the presence of, the compound of interest, the elution time of the compound of interest is "recognized" in step 410.

In operation block 412, peak areas obtained from a second chromatogram from the compound-quantitating/purity determining device 212 are associated with the specific peaks in the second chromatogram, and stored in memory. Moreover, elution times are likewise associated with each peak and stored in memory in step 414. In step 416, the amount of each compound present is determined from the peak areas, using, for example, the expression [1] presented earlier in this specification. It should be understood that operations 402–410, and operations 412–416 can be carried out in parallel.

In block 420, a peak appearing in the second chromatogram and representative of the compound of interest is identified. Such identification is performed by matching the elution time of the compound of interest, as obtained from the first chromatogram, to a peak from the second chromatogram having the same elution time. Substantially simultaneous peak detection in the compound-determining device 210 and compound-quantitating/purity determining device 212, as taught by the applicants (see steps 106 & 108 of FIG. 1), makes the applicants' novel cross-identification operation possible. Such cross-identification of a compound between different analytical devices via simultaneous peak detection provides the art with a means for analyzing samples at a hitherto unattainable rapid rate.

Once the compound of interest is identified in the second chromatogram, that compound is "recognized" as being present in a specific amount, as per operation block 422. The purity of the compound of interest is determined in block 424, substituting the information obtained in blocks 416 and 422 into expression [2] presented earlier in this specification. Finally, a report is prepared, utilizing information obtained in various functional blocks, such as, for example, block 408 (confirmation), block 422 (amount), and block 424 (purity).

Figure 5:
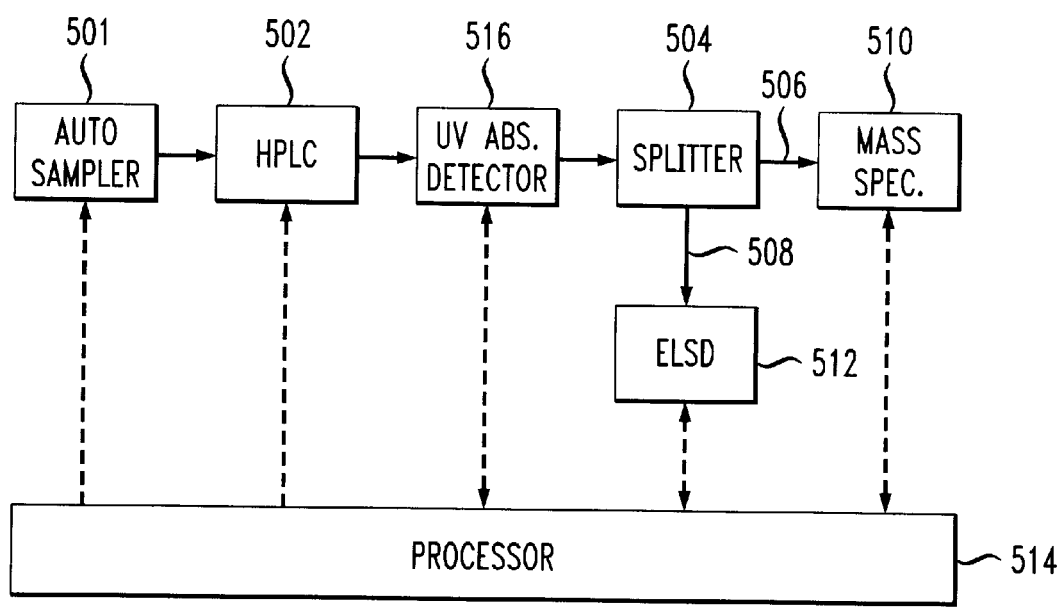
FIG. 5 shows a first embodiment of the apparatus shown in FIG. 2.

FIG. 5 shows an apparatus 500 comprising exemplary analytical devices suitable for carrying out the present invention. The apparatus 500 shown in FIG. 5 includes an auto sampler 501, such as, for example, a model Series 200 Autosampler, available from The Perkin Elmer Corporation of Foster City, Calif. or a model 215 Liquid Handling System, available from Gilson Inc. of Middleton, Wis. The autosampler 501 provides a mixture for analysis to an HPLC 502, such a model HP 1100 Series LC available from Hewlett-Packard Company of Wilmington, Del. Autosampler operation is optionally under the control of an appropriately-programmed general purpose processor or a hardwired special-purpose processor 514. Programming software for equipment control is usually available from equipment vendors. For example, PE Sciex Open MS™, available from PE Sciex, is operable to control its Autosampler, such as the aforementioned Series 200 Autosampler. Alternatively, autosampler operation can be controlled using more broadly-applicable software, such as MassChrom™ by PE Sciex.

The compounds present in the mixture are separated by the HPLC 502, producing an eluent having a time-varying composition. In one embodiment, the BPLC is operated in reverse phase mode. The composition of the solvent is varied over time to produce a gradient of eluting strength. The BPLC 502 is optionally controlled by the processor 514. The eluent from the HPLC 502 is delivered to optional UV absorbance detector 516, such as a model HP 1100 Diode-Array Detector available from Hewlett-Packard. The UV absorbance detector 516 provides additional analytical information, such as spectral absorbance information, useful for a secondary confirmation of peak and compound presence.

After optional UV detection, the eluent is split into two streams by the splitter 504. A first stream is delivered, via conduit 506, to a mass spectrograph 510, such as a model API 150 EX available from Perkin Elmer. The mass spectrograph 510 is operable to calculate molecular weight, which is used to confirm the identity of a compound of interest. A second stream is delivered, via conduit 508, to an ELSD 512, such as the Sedex Models 55 and 65 detectors available from Sedere of Alfortville, France. The ELSD provides quantitative information about the compounds in the sample. In one embodiment, the eluent is split, volumetrically, in a ratio of about 1:3 to the mass spectrograph 510 and ELSD 512, respectively.

In the embodiment illustrated in FIG. 5, the mass spectrograph 510 and the ELSD 512 are controlled by the processor 514. It should be appreciated that the ability to control analytical equipment in this manner may vary with the particular model or version of such equipment being used. MassChrom™ data software, previously described, is used for autosampler and analytical equipment operation, data acquisition, and some post run processing. AppleScript™ is used for performing some of the operations shown in the flow chart in FIG. 4, including compound identification, quantitation and purity determination.

Although specific embodiments of this invention have been described herein, it is to be understood that these embodiments are merely illustrative of the principles of this invention. Numerous and varied modifications may occur to, and be implemented by, those of ordinary skill in the art in view of the present teachings without departing from the scope and the spirit of the invention. For example, the present method for cross-correlating the operation of two devices via simultaneous peak detection can be used to cross-correlate the operation of analytical devices other than a compound-identifying device and a compound-quantitating/purity-determining device for purposes other than compound identification, quantitation and purity determination.

We claim:

1. A method for identifying and quantitating at least a first compound in a mixture having a plurality of compounds, comprising the steps of:

(A) separating the compounds, the separated compounds forming an eluent having a time-varying composition, the eluent representable by a chromatogram having a plurality of positionally-separated peaks extending above a baseline, the peaks corresponding to the compounds of the mixture, the position of each peak corresponding to an elution time for a corresponding compound;

(B) splitting the eluent into a first portion that is delivered to a compound-identifying device and a second portion that is delivered to a compound quantitating/purity-determining device;

(C) detecting a first compound in the first portion using the compound-identifying device, representing the first compound as a first peak extending above a baseline and having a first elution time in a first chromatogram, and identifying the first peak as corresponding to the first compound;

(D) detecting the first compound in the second portion using the compound quantitating/purity-determining device, representing the first compound as a second peak extending above a baseline and having a second elution time in a second chromatogram, and determining that the second peak corresponds to the first compound; and (E) quantitating the first compound using the second peak; wherein, the first compound in the first and second portions are detected substantially contemporaneously.

2. The method of claim 1, wherein step (D) comprises determining that the second peak corresponds to the first compound by matching the second elution time to the first elution time, the first and second elution times being substantially the same.

3. The method of claim 2, wherein step (A) comprises adsorbing the compounds of the mixture on to a solid stationary phase and desorbing the compounds of the mixture from the solid stationary phase, wherein each compound in the mixture adsorbs/desorbs at a unique rate, thereby determining a unique elution time for each compound.

4. The method of claim 3, wherein the operations of adsorbing the compounds of the mixture onto a solid stationary phase and desorbing the compounds of the mixture from the solid stationary phase comprise separating the compounds of the mixture using high performance liquid chromatography.

5. The method of claim 2, wherein step (E) comprises quantitating the first compound by determining the area under the second peak, and further determining the area under other peaks appearing in the second chromatogram.

6. The method of claim 5, further comprising correlating the area under the second peak and said other peaks to mass, and determining a purity of the first compound according to the expression: $P=(m_i/\Sigma m_i) \times 100$, wherein P is the percentage purity of the first compound, $m_i$ is the mass of the first compound in the mixture, and $\Sigma m_i$ is the mass of all compounds in the mixture.

7. The method of claim 1, wherein step (C) comprises using a mass spectrometer for detecting the first compound and confirming its identity as the first compound.

8. The method of claim 1, wherein step (D) comprises using an evaporative light scattering detector for detecting the first compound.

9. The method of claim 1, wherein, step (B) comprises splitting the eluent so that no more than about 25 weight percent of the eluent is apportioned to the first portion, and at least about 75 volume percent of the eluent is apportioned to the second portion.

10. The method of claim 1, and further comprising the step of using a UV detector to obtain spectral absorbance data for compounds in the eluent.

11. A method for correlating the identity of a first compound in a first mixture of compounds between different analytical devices, comprising the steps of:

(A) forming a second mixture having a time-varying composition, the second mixture comprising the same compounds as the first mixture;

(B) splitting the second mixture into a first and a second portion, the first and second portions having the same time-varying composition;

(C) detecting the first compound in the first portion using a first analytical device, representing the first compound as a first peak extending above a baseline and having a first elution time in a first chromatogram, and identifying the first peak as corresponding to the first compound;

(D) detecting the first compound in the second portion using a second analytical device, representing the first compound as a second peak extending above a baseline and having a second elution time in a second chromatogram, and determining that the second peak corresponds to the first compound; wherein, the first compound in the first and second portions are detected substantially contemporaneously.

* * * * *